(12) United States Patent
Resconi et al.

(10) Patent No.: US 7,964,679 B2
(45) Date of Patent: Jun. 21, 2011

(54) PROCESS FOR THE POLYMERIZATION OF ALPHA OLEFINS

(75) Inventors: Luigi Resconi, Ferrara (IT); Simona Guidotti, Bologna (IT); Iolanda Santoriello, Salerno (IT)

(73) Assignee: Basell Poliolefine Italia s.r.l., Milan (IT)

( * ) Notice: Subject to any disclaimer, the term of this patent is extended or adjusted under 35 U.S.C. 154(b) by 646 days.

(21) Appl. No.: 11/919,843

(22) PCT Filed: Apr. 12, 2006

(86) PCT No.: PCT/EP2006/061545
§ 371 (c)(1),
(2), (4) Date: Feb. 4, 2008

(87) PCT Pub. No.: WO2006/117285
PCT Pub. Date: Nov. 9, 2006

(65) Prior Publication Data
US 2008/0269439 A1 Oct. 30, 2008

Related U.S. Application Data

(60) Provisional application No. 60/679,141, filed on May 9, 2005.

(30) Foreign Application Priority Data

May 3, 2005 (EP) .................................. 05103663

(51) Int. Cl.
*C08F 4/6592* (2006.01)
*C08F 10/08* (2006.01)
*C07F 17/00* (2006.01)

(52) U.S. Cl. ........ 526/127; 526/160; 526/161; 526/170; 526/172; 526/348; 526/348.6; 526/943

(58) Field of Classification Search .................. 526/160, 526/170, 127, 348, 348.6, 943
See application file for complete search history.

(56) References Cited

U.S. PATENT DOCUMENTS

| | | | |
|---|---|---|---|
| 4,178,272 A | 12/1979 | Meyer, Jr. et al. | |
| 5,698,487 A | 12/1997 | Sacchetti et al. | |
| 5,770,664 A * | 6/1998 | Okumura et al. | 526/127 |
| 5,770,753 A | 6/1998 | Küber et al. | |
| 5,786,432 A | 7/1998 | Küber et al. | |
| 5,840,644 A | 11/1998 | Küber et al. | |
| 6,051,727 A | 4/2000 | Küber et al. | |
| 6,242,544 B1 | 6/2001 | Küber et al. | |
| 6,255,506 B1 | 7/2001 | Küber et al. | |
| 6,306,996 B1 | 10/2001 | Cecchin et al. | |
| 6,399,533 B2 | 6/2002 | Sacchetti et al. | |
| 6,444,833 B1 | 9/2002 | Ewen et al. | |
| 6,492,539 B1 | 12/2002 | Bingel et al. | |
| 6,559,252 B1 | 5/2003 | Horton et al. | |
| 6,608,224 B2 | 8/2003 | Resconi et al. | |
| 6,635,779 B1 | 10/2003 | Ewen et al. | |
| 6,841,501 B2 | 1/2005 | Resconi et al. | |
| 6,878,786 B2 | 4/2005 | Resconi et al. | |
| 6,949,614 B1 | 9/2005 | Schottek et al. | |

(Continued)

FOREIGN PATENT DOCUMENTS

DE 19917985 10/2000

(Continued)

OTHER PUBLICATIONS

C. Carman et al., "Monomer Sequence Distribution in Ethylene-Propylene Rubber Measured by $^{13}$C NMR. 3. Use of Reaction Probability Model," *Macromolecules*, vol. 10(3), p. 536-544 (1977).

(Continued)

*Primary Examiner* — Roberto Rabago
(74) *Attorney, Agent, or Firm* — Dilworth IP LLC

(57) ABSTRACT

A process for preparing 1-butene polymers, comprising polymerizing 1-butene or copolymerizing 1-butene with ethylene, propylene or an alpha-olefin of formula $CH_2$=CHT wherein T is a $C_3$-$C_{10}$ alkyl group, in the presence of a catalyst system obtainable by contacting:

A) a metallocene compound belonging to formula (I):

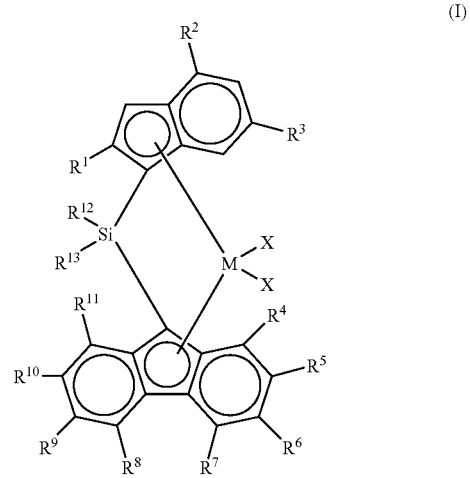

(I)

wherein
M is zirconium titanium or hafnium;
X, equal to or different from each other, is a hydrogen atom, a halogen atom, a hydrocarbon radical, optionally containing heteroatoms; $R^4$, $R^5$, $R^6$, $R^7$, $R^8$, $R^9$, $R^{10}$, $R^{11}$, $R^{12}$ and $R^{13}$ are hydrogen atoms, or $C_1$-$C_{40}$ hydrocarbon radicals optionally containing heteroatoms;
$R^1$, $R^2$ and $R^3$, are linear or branched, $C_1$-$C_{20}$-alkyl radicals, optionally containing heteroatoms:
B) a lumoxane or a compound capable of forming an alkyl metallocene cation; and optionally
C) organo aluminum compound.

6 Claims, No Drawings

U.S. PATENT DOCUMENTS

| | | |
|---|---|---|
| 6,953,829 B2 | 10/2005 | Kratzer et al. |
| 6,963,017 B2 | 11/2005 | Bingel et al. |
| 7,038,070 B2 | 5/2006 | Bingel et al. |
| 7,053,160 B1 | 5/2006 | Bingel et al. |
| 7,101,940 B2 | 9/2006 | Schottek et al. |
| 7,112,638 B2 | 9/2006 | Nifant'ev et al. |
| 7,141,527 B1 | 11/2006 | Van Baar et al. |
| 7,141,637 B2 | 11/2006 | Elder et al. |
| 7,314,903 B2 | 1/2008 | Resconi et al. |
| 2003/0149199 A1 | 8/2003 | Schottek et al. |
| 2004/0132612 A1 | 7/2004 | Resconi et al. |
| 2006/0020096 A1 | 1/2006 | Schottek et al. |
| 2006/0052553 A1 | 3/2006 | Resconi et al. |
| 2006/0235173 A1 | 10/2006 | Resconi |
| 2007/0155919 A1 | 7/2007 | Okumura et al. |
| 2007/0260023 A1 | 11/2007 | Jones et al. |
| 2007/0276095 A1 | 11/2007 | Resconi et al. |

FOREIGN PATENT DOCUMENTS

| | | |
|---|---|---|
| DE | 19962814 | 6/2001 |
| DE | 19962910 | 7/2001 |
| EP | 172961 | 3/1986 |
| EP | 576970 | 1/1994 |
| EP | 633272 | 1/1995 |
| EP | 775707 | 5/1997 |
| EP | 938491 | 9/1999 |
| GB | 1575894 | 10/1980 |
| JP | 4016851 | 1/1992 |
| JP | 4016853 | 1/1992 |
| JP | 4016854 | 1/1992 |
| JP | 4031868 | 2/1992 |
| WO | 91/02012 | 2/1991 |
| WO | 92/00333 | 1/1992 |
| WO | 95/32995 | 12/1995 |
| WO | 98/40331 | 9/1998 |
| WO | 99/21899 | 5/1999 |
| WO | 99/45043 | 9/1999 |
| WO | 00/31090 | 6/2000 |
| WO | 01/21674 | 3/2001 |
| WO | 01/44318 | 6/2001 |
| WO | 01/47939 | 7/2001 |
| WO | 01/48034 | 7/2001 |
| WO | 01/32764 | 8/2001 |
| WO | 02/102811 | 12/2002 |
| WO | 03/045964 | 6/2003 |
| WO | 03/050131 | 6/2003 |
| WO | 2004/005360 | 1/2004 |
| WO | 2004/050724 | 6/2004 |
| WO | 2004/099269 | 11/2004 |
| WO | 2005/023889 | 3/2005 |
| WO | 2005/058916 | 6/2005 |
| WO | 2005/095468 | 10/2005 |
| WO | 2005/095473 | 10/2005 |
| WO | 2005/095474 | 10/2005 |
| WO | 2005/118654 | 12/2005 |
| WO | 2006/097497 | 9/2006 |
| WO | 2006/097500 | 9/2006 |
| WO | 2006/100258 | 9/2006 |
| WO | 2006/100269 | 9/2006 |
| WO | 2006/120177 | 11/2006 |

OTHER PUBLICATIONS

M. Kakugo et al., "$^{13}$C NMR Determination of Monomer Sequence Distribution in Ethylene-Propylene Copolymers Prepared with $\delta$-TiCl$_3$-Al(C$_2$H$_5$)$_2$Cl," *Macromolecules*, vol. 15(4), p. 1150-1152 (1982).

A. Rossi et al., "End Groups in 1-Butene Polymerization via Methylaluminoxane and Zirconocene Catalyst," *Macromolecules*, vol. 28(6), p. 1739-1749 (1995).

N. Naga et al., "Effect of co-catalyst system on $\alpha$-olefin polymerization with *rac* -and *meso*- [dimethylsilylenebis(2,3,5-trimethylcyclopentadienyl)]zirconium dichloride," *Macromol. Rapid Commun.*, vol. 18, p. 581-589 (1997).

L. Resconi et al., "$C_1$-Symmetric Heterocyclic Zirconocenes as Catalysts for Propylene Polymerization, 2; *ansa*-Zirconocenes with Linked Dithienocyclopentadienyl-Substituted Indenyl Ligands," *Macromol. Chem. Phys.*, vol. 206, p. 1405-1438 (2005).

C. Cobzaru et al., "Novel High and Ultrahigh Molecular Weight Poly(propylene) Plastomers by Asymmetric Hafnocene Catalysts," *Macromol. Chem. Phys.*, vol. 206, p. 1231-1240 (2005).

L. Resconi et al., "Selectivity in Propene Polymerization with Metallocene Catalysts," *Chem. Rev.*, vol. 100(4), p. 1253-1345 (2000).

\* cited by examiner

PROCESS FOR THE POLYMERIZATION OF ALPHA OLEFINS

This application is the U.S. national phase of International Application PCT/EP2006/061545, filed Apr. 12, 2006, claiming priority to European Patent Application 05103663.0 filed May 3, 2005, and the benefit under 35 U.S.C. 119(e) of U.S. Provisional Application No. 60/679,141, filed May 9, 2005; the disclosures of International Application PCT/EP2006/061545, European Patent Application 05103663.0 and U.S. Provisional Application No. 60/679,141, each as filed, are incorporated herein by reference.

The present invention relates to a process for polymerizing alpha olefins especially 1-butene by using a bridged indenyl fluorenyl metallocene compound. Furthermore the present invention relates to the new metallocene compound.

1-Butene polymers are well known in the art. In view of their good properties in terms of pressure resistance, creep resistance, and impact strength, they are widely used for example in the manufacture of pipes for metal pipe replacement, easy-open packaging and films.

The 1-butene (co)polymers are generally prepared by polymerizing 1-butene in the presence of $TiCl_3$ based catalyst components together with diethylaluminum chloride (DEAC) as cocatalyst. In some cases mixtures of diethyl aluminum iodide (DEAI) and DEAC are used. The polymers obtained, however, generally do not show satisfactory mechanical properties. Furthermore, in view of the low yields obtainable with the $TiCl_3$ based catalysts, the 1-butene polymers prepared with these catalysts have a high content of catalyst residues (generally more than 300 ppm of Ti) which lowers the properties of the polymers and makes necessary to carry out a subsequent deashing step.

1-Butene (co)polymers can also be obtained by polymerizing the monomers in the presence of a stereospecific catalyst comprising: (A) a solid component comprising a Ti compound and an electron-donor compound supported on $MgCl_2$; (B) an alkylaluminum compound and, optionally, (C) an external electron-donor compound. A process of this type is disclosed in EP-A-172961 and WO99/45043.

Recently metallocene compounds have been used for producing 1-butene polymers. Recently, metallocene compounds have been proposed for producing 1-butene polymers. In Macromolecules 1995, 28, 1739-1749, rac-dimethylsilylbis(4,5,6,7-tetrahydro-1-indenyl)zirconium dichloride and methylaluminoxane have been used for polymerizing 1-butene. The yield of the process is not indicated and the molecular weight of the obtained polymer (Mn) is very low. In Macromol. Rapid Commnun. 18, 581-589 (1997), rac- and meso-[dimethylsilylbis(2,3,5-trimethyl-cyclopentadienyl)]zirconium dichloride have been used for the polymerization of 1-butene. The yields of the process and the molecular weight of the obtained polymers are rather low.

Better results in terms of yield of the process, isotacticity and molecular weight of the obtained polymer have been obtained by using the metallocene compound described in WO 2004/099269. The class of the metallocene compound used in this document contains an heterocyclic ring fused to the central cyclopentadienyl moiety. This class of compounds is difficult to synthesize and the synthesis usually requires several steps. Therefore the better results in the polymerization process are paid with the difficulty to synthesize the metallocene compound.

There is therefore the need of a polymerization process that uses a metallocene compound easy to synthesize and that allows to produce 1-butene polymers having high molecular weights in good yields.

Thus, according to a first aspect, the present invention provides a process for preparing 1-butene polymers, said process comprising polymerizing 1-butene or copolymerizing 1-butene with ethylene, propylene or an alpha-olefin of formula $CH_2=CHT$ wherein T is a $C_3$-$C_{10}$ alkyl group, in the presence of a catalyst system obtainable by contacting:

A) a metallocene compound belonging to the following formula (X):

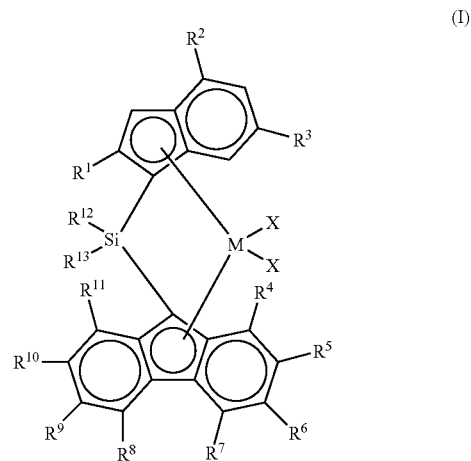

wherein

M is zirconium, titanium or hafnium; preferably M is zirconium;

X, equal to or different from each other, is a hydrogen atom, a halogen atom, a R, OR, OR'O, $OSO_2CF_3$, OCOR, SR, $NR_2$ or $PR_2$ group wherein R is a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing heteroatoms belonging to groups 13-17 of the Periodic Table of the Elements; and R' is a $C_1$-$C_{20}$-alkylidene, $C_6$-$C_{20}$-arylidene, $C_7$-$C_{20}$-alkylarylidene, or $C_7$-$C_{20}$-arylalkylidene radical; preferably X is a hydrogen atom, a halogen atom, a OR'O or R group; more preferably X is chlorine or a methyl radical;

$R^4$, $R^5$, $R^6$, $R^7$, $R^8$, $R^9$, $R^{10}$, and $R^{11}$, equal to or different from each other, are hydrogen atoms, or $C_1$-$C_{40}$ hydrocarbon radicals optionally containing heteroatoms belonging to groups 13-17 of the Periodic Table of the Elements; two or more $R^4$, $R^5$, $R^6$, $R^7$, $R^8$, $R^9$, $R^{10}$, and $R^{11}$ can also optionally join to form one or more $C_4$-$C_{10}$ condensed saturated or unsaturated ring; preferably $R^4$, $R^5$, $R^6$, $R^7$, $R^8$, $R^9$, $R^{10}$, and $R^{11}$, equal to or different from each other, are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical, optionally containing one or more heteroatoms belonging to groups 13-17 of the Periodic Table of the Elements; more preferably $R^4$, $R^5$, $R^6$, $R^7$, $R^8$, $R^9$, $R^{10}$, and $R^{11}$ are hydrogen atoms;

$R^{12}$ and $R^{13}$, equal to or different from each other, are hydrogen atom or $C_1$-$C_{40}$ hydrocarbon radicals optionally containing heteroatoms belonging to groups 13-17 of the Periodic Table of the Elements; preferably $R^{12}$ and $R^{13}$ are $C_1$-$C_{10}$ alkyl or $C_6$-$C_{20}$ aryl radicals; more preferably they are methyl radicals;

$R^1$, $R^2$ and $R^3$, equal to or different from each other, are linear or branched, $C_1$-$C_{20}$-alkyl radicals, optionally containing heteroatoms belonging to groups 13-17 of the Periodic Table of the Elements; preferably $R^1$, $R^2$ and $R^3$, equal to or different from each other, are $C_1$-$C_{10}$-alkyl radicals; more preferably $R^2$ and $R^3$ are methyl, or ethyl radicals and $R^1$ is a methyl, ethyl or isopropyl radical; even more preferably $R^1$ is a methyl, ethyl;

B) an alumoxane or a compound capable of forming an alkyl metallocene cation; and optionally C) an organo aluminum compound.

A further object of the present invention is a metallocene compound of formula (I)

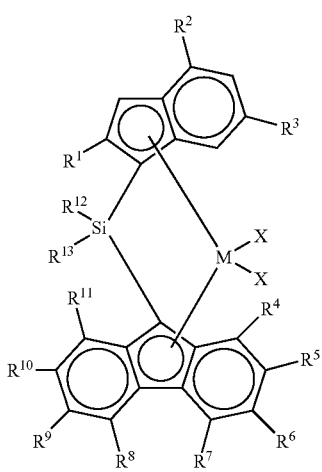

wherein
M, X, $R^1$, $R^2$, $R^3$, $R^4$, $R^5$, $R^6$, $R^7$, $R^8$, $R^9$, $R^{10}$, $R^{11}$, $R^{12}$, $R^{13}$ have been described above.

A still further object of the present invention is the ligand of formula (II) and/or its double bonds isomer suitable for the obtainment of the metallocene compound of formula (I)

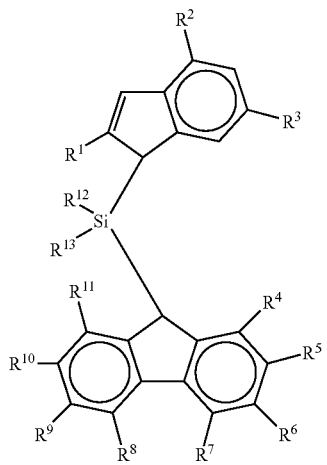

wherein
$R^1$, $R^2$, $R^3$, $R^4$, $R^5$, $R^6$, $R^7$, $R^8$, $R^9$, $R^{10}$, $R^{11}$, $R^{12}$, $R^{13}$ have been described above.

The metallocene compounds of formula (I) can be obtained with a process comprising the steps of reacting the dianion of the ligand of formula (II) with a suitable transition metal source such as metal tetrahalide as for example zirconium tetrachloride. The dianion can be obtained for example by the deprotonation of the ligand of formula (II), for example by using an organolithium compound such as butyl or methyl lithium.

The ligand of formula (II) can be easily prepared starting from the cyclopentadienyl moieties of formulas (III) and (IV)

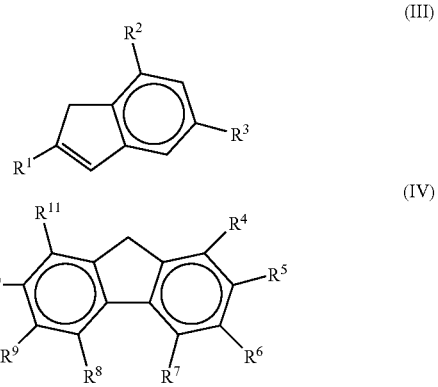

$R^1$, $R^2$, $R^3$, $R^4$, $R^5$, $R^6$, $R^7$, $R^8$, $R^9$, $R^{10}$, $R^{11}$, $R^{12}$, $R^{13}$ have been described above with a process comprising the following steps:

a) Contacting the compound of formula (III) and/or its double bond isomers with a base selected from $T_jB$, $TMgT^1$, sodium and potassium hydride, metallic sodium and potassium; wherein B is an alkaline or alkali-earth metal; and j is 1 or 2, j being equal to 1 when B is an alkaline metal, preferably lithium, and j being equal to 2 when B is an alkali-earth metal; T is a linear or branched, cyclic or acyclic, $C_1$-$C_{20}$-alkyl, $C_6$-$C_{20}$-aryl, $C_7$-$C_{20}$-alkylaryl or $C_7$-$C_{20}$-arylalkyl radical, optionally containing one or more Si or Ge atoms; preferably T is methyl or butyl radical; $T^1$ is an halogen atom or a group OR''' wherein R''' is a linear or branched, cyclic or acyclic, $C_1$-$C_{40}$-alkyl, $C_6$-$C_{40}$-aryl, $C_7$-$C_{40}$-alkylaryl or $C_7$-$C_{40}$-arylalkyl radical, optionally containing one or more heteroatoms belonging to groups 13-17 of the Periodic Table of the Elements; preferably $T^1$ is an halogen atom, more preferably bromine, and wherein the molar ratio between said base and the compound of the formula (III) is at least 1:1; excess of said base can be used;

b) contacting the anionic compound obtained in step a) with a compound of formula $SiR^{12}R^{13}Y_2$ wherein $R^{12}$ and $R^{13}$ are defined as above and Y is chlorine, bromine and iodine, preferably Y is chlorine or bromine; to form a compound of formula (IIIa)

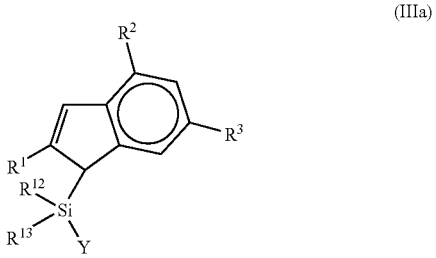

c) contacting the compound of formula (IIIa) with the anionic derivative of compound of formula (IV) obtained by contacting the compound of formula (IV)

with a base selected from T$_j$B, TMgT$^1$, sodium and potassium hydride, metallic sodium and potassium as described in step a) for compound of formula (III).

The above process can be also carried out by using the compound of formula (IV) in steps a) and b) to form the compound of formula (IVa)

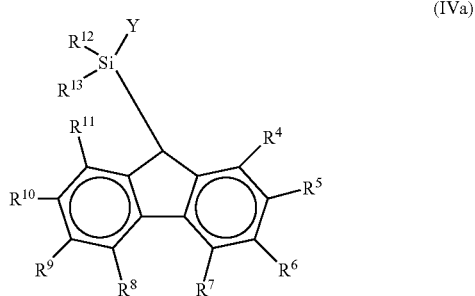

(IVa)

and the subsequent contact with the anionic derivative of compound of formula (III) as in step c). The above processes are preferably carried out in an aprotic solvent, either polar or apolar. Said aprotic solvent is preferably an aromatic or aliphatic hydrocarbon, optionally halogenated, or an ether; more preferably it is selected from benzene, toluene, pentane, hexane, heptane, cyclohexane, dichloromethane, diethylether, tetrahydrofurane and mixtures thereof. The above process is carried out at a temperature ranging from −100° C. to +80° C., more preferably from −20° C. to +70° C.

Alumoxanes used as component B) can be obtained by reacting water with an organo-aluminium compound of formula H$_j$AlU$_{3-j}$ or H$_j$Al$_2$U$_{6-j}$, where U substituents, same or different, are hydrogen atoms, halogen atoms, C$_1$-C$_{20}$-alkyl, C$_3$-C$_{20}$-cycloalkyl, C$_6$-C$_{20}$-aryl, C$_7$-C$_{20}$-alkylaryl or C$_7$-C$_{20}$-arylalkyl radical, optionally containing silicon or germanium atoms with the proviso that at least one U is different from halogen, and j ranges from 0 to 1, being also a non-integer number. In this reaction the molar ratio of Al/water is preferably comprised between 1:1 and 100:1. The molar ratio between aluminium and the metal of the metallocene generally is comprised between about 10:1 and about 20000:1, and more preferably between about 100:1 and about 5000:1. The alumoxanes used in the catalyst according to the invention are considered to be linear, branched or cyclic compounds containing at least one group of the type:

wherein the substituents U, same or different, are described above.

In particular, alumoxanes of the formula:

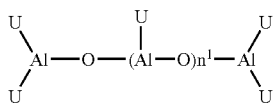

can be used in the case of linear compounds, wherein n$^1$ is 0 or an integer from 1 to 40 and the substituents U are defined as above, or alumoxanes of the formula:

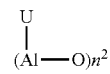

can be used in the case of cyclic compounds, wherein n$^2$ is an integer from 2 to 40 and the U substituents are defined as above. Examples of alumoxanes suitable for use according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO). Particularly interesting cocatalysts are those described in WO 99/21899 and in WO01/21674 in which the alkyl and aryl groups have specific branched patterns. Non-limiting examples of aluminium compounds according to WO 99/21899 and WO01/21674 are:
tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluoro-phenyl)-propyl]aluminium, tris[2-(4-chloro-phenyl)-propyl]aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl)aluminium, tris[2-(pentafluorophenyl)-propyl]aluminium, tris[2,2-diphenyl-ethyl]aluminium and tris[2-phenyl-2-methyl-propyl]aluminium, as well as the corresponding compounds wherein one of the hydrocarbyl groups is replaced with a hydrogen atom, and those wherein one or two of the hydrocarbyl groups are replaced with an isobutyl group.

Amongst the above aluminium compounds, trimethylaluminium (TMA), triisobutylaluminium (TIBAL), tris(2,4,4-trimethyl-pentyl)aluminium (TIOA), tris(2,3-dimethylbutyl)aluminium (TDMBA) and tris(2,3,3-trimethylbutyl)aluminium (TTMBA) are preferred.

Non-limiting examples of compounds able to form an alkylmetallocene cation are compounds of formula D$^+$E$^-$, wherein D$^+$ is a Brønsted acid, able to donate a proton and to react irreversibly with a substituent X of the metallocene of formula (I) and E$^-$ is a compatible anion, which is able to stabilize the active catalytic species originating from the reaction of the two compounds, and which is sufficiently labile to be able to be removed by an olefinic monomer. Preferably, the anion E$^-$ comprises of one or more boron atoms. More preferably, the anion E$^-$ is an anion of the formula BAr$_4$$^{(-)}$, wherein the substituents Ar which can be identical or different are aryl radicals such as pentafluorophenyl or bis(trifluoromethyl)phenyl. Tetrakis-pentafluorophenyl borate is particularly preferred examples of these compounds are described in WO 91/02012. Moreover, compounds of the formula BAr$_3$ can conveniently be used. Compounds of this type are described, for example, in the published International patent application WO 92/00333. Other examples of compounds able to form an alkylmetallocene cation are compounds of formula BAr₃P wherein P is a substituted or unsubstituted pyrrol radicals. These compounds are described in WO01/62764. Other examples of cocatalyst can be found in EP 775707 and DE 19917985. Compounds containing boron atoms can be conveniently supported according to the description of DE-A-19962814 and DE-A-19962910. All these compounds containing boron atoms can be used in a molar ratio between boron and the metal of the metallocene comprised between about 1:1 and about 10:1; preferably 1:1 and 2.1; more preferably about 1:1.

Non limiting examples of compounds of formula $D^+E^-$ are:
Tributylammoniumtetrakis(pentafluorophenyl)borate,
Tributylammoniumtetrakis(pentafluorophenyl)aluminate,
Tributylammoniumtetrakis(trifluoromethylphenyl)borate,
Tributylammoniumtetrakis(4-fluorophenyl)borate,
N,N-Dimethylbenzylammonium-tetrakis(pentafluorophenylborate,
N,N-Dimethylhexylammonium-tetrakis(pentafluorophenyl)borate,
N,N-Dimethylaniliniumtetrakis(pentafluorophenyl)borate,
N,N-Dimethylaniliniumtetrakis(pentafluorophenyl)aluminate,
N,N-Dimethylbenzylammonium-tetrakis(pentafluorophenylborate,
N,N-Dimethylhexylammonium-tetrakis(pentafluorophenyl)borate,
Di(propyl)ammoniumtetrakis(pentafluorophenyl)borate,
Di(cyclohexyl)ammoniumtetrakis(pentafluorophenyl)borate,
Triphenylcarbeniumtetrakis(pentafluorophenyl)borate,
Triphenylcarbeniumtetrakis(pentafluorophenyl)aluminate,
Ferroceniumtetrakis(pentafluorophenyl)borate,
Ferroceniumtetrakis(pentafluorophenyl)aluminate.
Triphenylcarbeniumtetrakis(pentafluorophenyl)borate, and
N,N-Dimethylaniliniumtetrakis(pentafluorophenyl)borate.

Organic aluminum compounds used as compound C) are those of formula $H_jAlU_{3-j}$ or $H_jAl_2U_{6-j}$ described above.

The polymerization process of the present invention can be carried out in liquid phase, optionally in the presence of an inert hydrocarbon solvent, or in gas phase. Said hydrocarbon solvent can be either aromatic (such as toluene) or aliphatic (such as propane, hexane, heptane, isobutane, cyclohexane, isododecane, and 2,2,4-trimethylpentane). Preferably, the polymerization process of the present invention is carried out by using liquid 1-butene as polymerization medium. The polymerization temperature preferably ranges from 0° C. to 250° C.; preferably comprised between 20° C. and 150° C. and, more particularly between 50° C. and 90° C. The molecular weight distribution can be varied by using mixtures of different metallocene compounds or by carrying out the polymerization in several stages which differ as to the polymerization temperature and/or the concentrations of the molecular weight regulators and/or the monomers concentration. Moreover by carrying out the polymerization process by using a combination of two different metallocene compounds of formula (I) a polymer endowed with a broad melting is produced. The polymerization yield depends on the purity of the transition metal organometallic catalyst compound (A) in the catalyst, therefore, said compound can be used as such or can be subjected to purification treatments before use.

The polymerization process of the present invention can be carried out in the presence of hydrogen in order to increase the yield.

When 1-butene is copolymerized with ethylene, propylene or alpha olefins of formula $CH_2=CHT$ wherein T is a $C_3$-$C_{10}$ alkyl group, a copolymer having a content of comonomer derived units of up to 50% by mol can be obtained, preferably up to 20% by mol, more preferably from 0.2% by mol to 15% by mol. Examples of alpha-olefins of formula $CH_2=CHT$ are 1-pentene, 4-methyl-1-pentene, 1-hexene, 1-octene, 4,6-dimethyl-1-heptene, 1-decene, 1-dodecene. Preferred comonomer to be used in the process according to the present invention are ethylene, propylene and 1-hexene.

With the process of the present invention it is possible to obtain 1-butene polymers having high molecular weight, measured in terms of their intrinsic viscosity (I.V. or Mv) and in high yields. The metallocene compound of formula (I) can also be used for the (co)polymerization of alpha olefins such as ethylene and propylene, and higher alpha olefins. Therefore a further object of the present invention is a process for the polymerization of alpha olefins comprising contacting, under polymerization conditions, one or more of said alpha olefins with a catalyst system obtainable by contacting:

A) the metallocene compound of formula (I)
B) an alumoxane or a compound capable of forming an alkyl metallocene cation; and optionally
C) an organo aluminum compound.

Preferred alpha olefins are $C_2$-$C_{20}$ alpha olefins such as ethylene, propylene, 1-butene 1-pentene, 4-methyl-1-pentene, 1-hexene, 1-octene, 4,6-dimethyl-1-heptene, 1-decene, 1-dodecene.

A still further object of the present invention is a catalyst system for the polymerization of alpha olefins obtainable by contacting:

A) the metallocene compound of formula (I)
B) an alumoxane or a compound capable of forming an alkyl metallocene cation; and optionally
C) an organo aluminum compound.

The following examples are given to illustrate and not to limit the invention.

EXAMPLES

Polybutene Characterization

Molecular weights. The viscosity average molecular weights were determined from the intrinsic viscosity values measured in tetrahydronaphthalene (THN) at 135° C., from the relationship: $<M_v>=(I.V./0.000178)\exp(1/0.725)$.

Thermal data. The melting points of the polymers ($T_m$) were measured by Differential Scanning Calorimetry (D.S.C.) on a Perkin Elmer DSC-1 calorimeter equipped with Pyris 1 software, previously calibrated against indium and zinc melting points. The weight of the samples in every DSC crucible was kept at 6.0±0.5 mg.

In order to obtain the melting point of form II, the weighted sample was sealed into aluminum pans and heated to 180° C. at 10° C./minute. The sample was kept at 180° C. for 5 minutes to allow a complete melting of all the crystallites, then cooled to 20° C. at 10° C./minute. After standing 2 minutes at 20° C., the sample was heated for the second time to 180° C. at 10° C./min. In this second heating run, the peak temperature was taken as the melting temperature of form II ($T_m$ II) and the area of the peak as its melting enthalpy ($\Delta H_f$).

Glass Transition Temperature ($T_g$)

The $T_g$ values were determined on a DSC30 Mettler instrument equipped with a cooling device, by heating the sample from 25° C. to 200° C. at 20° C./min, holding for 10 min at 200° C., cooling from 200° C. to −140° C., holding for 2 min at −140° C., heating from −140° C. to 200° C. at 20° C./min. The reported values are those determined from the flex of the glass transition in the second heating scan.

Polypropylene Analysis

The melting points (Tm) and heat of fusion (ΔHf) of the polymers were measured by Differential Scanning Calorimetry (DSC) on a Mettler or Perkin Elmer DSC-7 instruments, according to the standard method, on 5-10 mg samples sealed into aluminum pans and heated at 200° C. with a heating rate of 10° C./minute. The sample was kept at 200° C. for 2 minutes to allow a complete melting of all the crystallites, then cooled to 25° C. at 10° C./minute, then kept 2 minutes at 0° C., and then heated again up to 200° C. at 10° C./min. The peak temperature of the second melting was taken as the melting temperature (Tm) and the area as the melting enthalpy (ΔHf).

The average viscosity molecular weights were determined from the intrinsic viscosity of the samples, measured in tetrahydronaphthalene (THN) at 135° C.

General procedures. All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. Fluorene, $Me_2SiCl_2$, n-butyllithium, methyllithium and the solvents were used as received from Aldrich. The NMR spectra were obtained on a Bruker DPX 200 spectrometer operating in the Fourier transform mode at room temperature. The samples were dissolved in $CD_2Cl_2$ (Aldrich, 99.8 atom % D) stored over molecular sieves (4-5 Å). Preparation of the samples was carried out under nitrogen using standard inert atmosphere techniques. The residual peak of $CHDCl_2$ in the $^1H$ spectra (5.35 ppm) and the peak of the solvent in the $^{13}C$ spectra (the middle peak of $CD_2Cl_2$ at 53.80 ppm) were used as a reference. Proton spectra were acquired with a 15° pulse and 2 seconds of delay between pulses; 32 transients were stored for each spectrum. The carbon spectra were acquired with a 45° pulse and 6 s of delay between pulses; about 512 transients were stored for each spectrum.

Synthesis of dimethylsilyl(2,4,6-trimethylinden-1-yl) (9-fluorenyl)zirconium dichloride (A-1)

2,4,6-trimethylindan-1-one

A 500 μL, 3-neck rounded bottom flask equipped with a magnetic stirring bar and a reflux condenser, was charged under nitrogen with 71.16 g of $AlCl_3$ (0.53 mol) dissolved in 240 mL of chlorobenzene. At room temperature 28.38 mL of m-xylene (0.23 mol) were added dropwise obtaining a light yellow suspension. The flask was then cooled to 0° C. and 28.68 mL of 2-bromoisobutyryl bromide (0.23 mol) were slowly added. At the end of the addition a dark-red slurry was obtained. The reaction mixture was then allowed to warm up to room temperature (r.t.) and stirred for 2 hours. Then it was transferred into a flask containing a solution of 3/1 ice/37% HCl. The organic phase was extracted with $Et_2O$ (3×200 mL), the combined organic phases were dried over $Na_2SO_4$, filtered and the solvents were removed in vacuo to leave 37.48 g of an orange oil (yield 93.5%). The latter was used as such in the next step without further purification.

2,4,6-trimethylindan-1-ol 37.48 g of 2,4,6-trimethyl-indan-1-one (0.215 mol) were dissolved in 200 mL of EtOH in a 500 mL, 3-neck rounded bottom flask equipped with a magnetic stirring bar, a thermometer and a reflux condenser. $NaBH_4$ (15.01 g, 0.397 mol) was then slowly added keeping the temperature below 20° C. during the addition. The light yellow suspension was stirred at r.t. for 18 h. Then 100 mL of acetone were cautiously added (careful: exothermic reaction!) and subsequently the solvents removed giving a white solid. The latter was treated with 100 mL of water and extracted with toluene (2×150 mL). The water phase was further extracted with toluene, the organic phases were combined and washed with a 10% aqueous solution of $NH_4Cl$. After washing, the organic phase was dried over $Na_2SO_4$, filtered and evaporated to give 35.57 g of a yellow sticky solid: its $^1H$-NMR analysis showed the target product as 1.4/1 mixture of two diastereoisomers, contaminated by 5% wt. of starting indanone (yield 89.2%). The product was used as such in the next step without further purification.

2,4,6-trimethylindene

The 2,4,6-trimethyl-indan-1-ol, prepared as described above (35.57 g, 0.192 mol), 0.5 g of p-toluensulfonic acid monohydrate and 160 mL of toluene were placed in a 500 mL, 3-neck rounded bottom flask equipped with a magnetic stirring bar, a dean-Stark apparatus and a reflux condenser. The reaction mixture was heated at 80° C. for 3 h and 3.5 mL of water were collected. Then the reaction mixture was cooled to room temperature and treated with a saturated $NaHCO_3$ aqueous solution: the organic layer was separated, the aqueous layer extracted with $Et_2O$ and the organic phases collected. After drying over $Na_2SO_4$, the solvent was evaporated in vacuo giving 28.46 g of an orange oil, which resulted to be by NMR analysis the desired product (purity 93.7% by GC-MS) contaminated by 2.0% wt. of indanone, coming from the previous step (yield 87.8%). The product was used as such in the next step without further purification.

Chloro(2,4,6-trimethylindenyl)dimethylsilane

A 2.5 M n-BuLi solution in hexane (37.2 mL, 0.093 mol) was added dropwise at 0° C. under nitrogen to a solution of 14.00 g of 2,4,6-trimethylindene (0.088 mol) in 100 mL of $Et_2O$ in a 500 mL 3-necked round flask. During the addition a white suspension was formed. The mixture was then allowed to warm up to r.t. and stirred for 30 min, with final formation of a white suspension. Then a solution of $Me_2SiCl_2$ (11.28 mL, 0.093 mol.) in 30 mL of THF was cooled to 0° C. and slowly added to the lithium salt suspension, also cooled to 0° C. The reaction mixture was allowed to warm up to r.t. and stirred for 2 h with final formation of a light yellow suspension. Then the solvents were removed in vacuo and the residue was extracted with 150 mL of toluene to remove LiCl. The light yellow filtrate was brought to dryness in vacuo to give 21.53 g of a yellow oil: its $^1H$-NMR analysis showed the presence of the target product together with traces of starting 2,4,6-trimethyl-indene (yield 97.5%).

$^1H$-NMR ($CDCl_3$), ppm: 0.12 (s, 3H, Si—$CH_3$); 0.40 (s, 3H, Si—$CH_3$); 2.19 (s, 3H, $CH_3$ in 2); 2.34 (s, 3H, $CH_3$); 2.37 (s, 3H, $CH_3$); 3.51 (s, 1H, CH); 6.65 (m, 1H, Cp-H); 6.86 (s, 1H); 7.09 (s, 1H). The product was used as such in the next step without further purification.

(2,4,6-trimethylindenyl)(9-fluorenyl)dimethylsilane

A 2.5 M n-BuLi solution in hexane (16.75 mL, 41.88 mmol) was added dropwise at 0° C. under stirring to a solution of 6.63 g of fluorene (39.89 mmol) in 100 ml of $Et_2O$ in a 500 mL 3-necked round flask. The resulting orange solution was allowed to warm up to room temperature and stirred for 1.5 h. A solution of chloro(2,4,6-trimethyl-indenyl)dimethylsilane (10 g, 39.87 mmol) in 20 mL of THF was cooled to 0° C. and slowly added to the lithium salt solution, also previously cooled to 0° C. At the end of the addition a light brown suspension was obtained. The latter was allowed to warm up to room temperature and stirred for 1.5 h. Then the reaction mixture was evaporated under reduced pressure to give a brown sticky solid, which was treated at r.t. with 150 mL of toluene and then filtered to remove LiCl. The filtrate was dried in vacuo to give 16.42 g of a brown oil, which resulted to be the expected ligand contaminated by minor amounts of non identified by-products (crude yield quantitative). The product was used as such in the next step without further purification.

Dimethylsilyl(2,4,6-trimethylindenyl)(9-fluorenyl)zirconium dichloride

A 2.5 M n-BuLi solution in hexane (35.30 mL, 88.25 mmol) was added dropwise at 0° C. under stirring to a solution of 16.42 g of (2,4,6-trimethyl-indenyl)(9-fluorenyl)dimethylsilane (43.14 mmol) in 100 mL of $Et_2O$ in a 500 mL 3-necked round flask. The resulting orange-red solution was allowed to warm up to r.t. and stirred for 1 h. Then a slurry of 10.02 g of $ZrCl_4$ (43.00 mmol) in 100 mL of toluene was prepared, cooled to 0° C. and added to the lithium salt solution, previously cooled to 0° C. The reaction mixture was then allowed to warm up to r.t. and stirred for 2.5 h. The solvents were removed in vacuo to give a dark-red residue, which was treated at r.t. with 150 mL of toluene and then filtered on a G4 frit. The residue was further washed with toluene (50 mL), then dried in vacuo to give 14.89 g of a brick-red powder: $^1H$ NMR analysis of the latter showed it to be the desired complex. Mass balance indicates the presence of 24.5% wt. of LiCl (yield 48.3%).

An aliquot of this sample (ca. 3 g) was dissolved into 40 mL of a mixture THF/toluene=1/3 (v/v), stirred for 15 min and filtered over a G4 frit. The filtrate was discarded, while the residue was further washed with a small amount of toluene and then dried to give ca. 2 g of an orange powder. $^1H$-NMR analysis of this powder identified it as the pure target compound.

$^1H$ NMR ($CD_2Cl_2$), ppm: 1.44 (s, 3H); 1.57 (s, 3H); 2.22 (bs, 6H); 2.27 (s, 3H); 6.55 (s, 1H); 6.71 (bs, 1H); 7.39 (bs, 1H); 7.00 (ddd, J=1.17, 6.85, 8.61 Hz, H2'); 7.16÷7.42 (m, 2H); 7.60 (ddd, 1H); 7.74 (d, 10; 7.79 (d, 1H); 7.89 (d, 1H); 7.99 (d, 1H).

Synthesis of dimethylsilyl(2,4,7-trimethylinden-1-yl) (9-fluorenyl)zirconium dichloride (A-2)

2,4,7-trimethylindanone 6.66 g of p-xylene (62.10 mmol) were added at room temperature to a suspension of 10.51 g of $AlCl_3$ (78.0 mmol) in 40 ml of chlorobenzene under nitrogen; the so obtained yellow suspension was cooled to 0° C. and 6.50 ml of 2-bromoisobutyrylbromide (52.6 mmol, $AlCl_3$/p-xylene/2-bromoisobutyrylbromide=1.5/1.2/1.0) were added dropwise in about 2 min. The flask is connected to a water trap in which the produced HBr gas is neutralized with a base. At the end of the addition, the solution was allowed to reach ambient temperature. The so obtained red solution was stirred for 2 h. The reaction mixture was transferred into a flask containing 30 g of ice and 10 ml of 37% HCl, stirred for 15 min, then the organic layer was separated, and the aqueous layer washed with $Et_2O$ (2×100 ml). The combined organic layers were washed with a saturated solution of $NaHCO_3$ in water, then with $H_2O$. The solution was dried over $Na_2SO_4$ and then all volatiles were removed in vacuo to leave a slightly yellow oil (8.95 g, yield 98%).

$^1H$-NMR ($CDCl_3$), ppm: 1.27 (d, 3H, $CH_3$); 2.28 (s, 3H, $CH_3$); 2.59 (s, 3H, $CH_3$); 2.59-2.69 (m, 2H, $CH+CH_2$); 3.17-3.29 (m, 1H, $CH_2$); 7.00 (d, 1H); 7.22 (d, 1H).

2,4,7-trimethylindan-1-ol 8.95 g of 2,4,7-trimethylindanone (51.4 mmol) were dissolved in 70 ml of EtOH; the solution was cooled to 0° C. and 2.00 g of $NaBH_4$ (51.8 mmol) were added to it in small aliquots. At the end of the addition, the reaction mixture was allowed to reach ambient temperature and then heated at 50° C. for 3 hours and 30 min. The reaction mixture was cooled to 0° C., and 50 ml of acetone were slowly (careful: exothermic reaction!) added to it to deactivate the residual borohydride. All volatiles were then removed in vacuo, the white solid obtained was treated with 50 ml of $1H_2O$ and stirred for 30 min. The organic layer was extracted with $Et_2O$ (2×100 ml), washed with $H_2O$, dried and essiccated in vacuo to leave 9.06 g of a white solid (100%).

2,4,7-trimethylindene 9.06 g of 2,4,7 trimethylindanol (51.4 mmol) were dissolved in 100 ml of toluene in a 250 ml, 2-neck flask equipped with magnetic stirring bar, Dean-Stark separator and bubble condenser. 0.15 g of p-toluenesulphonic acid monohydrate (0.78 mmol, 0.015 eq) were added, and the solution was heated to reflux, distilling the toluene-$H_2O$ azeotrope. After about 2 h, the temperature increased toward the boiling point of toluene, and after a few drops of pure toluene distillate, the reaction was stopped by cooling to room temperature and treating the solution with 100 ml of saturated $NaHCO_3$ aqueous solution. The organic phase was extracted with $Et_2O$ with the standard procedure, the combined organic phases were washed with $H_2O$ and then dried with $Na_2SO_4$. After filtration, the solvents were evaporated under reduced pressure to give 7.24 g of an off-white waxy product (yield: 89%).

$^1H$-NMR ($CDCl_3$), ppm: 2.19 (d, 3H, J=0.98 Hz, $CH_3$); 2.30 (s, 3H, $CH_3$); 2.36 (s, 3H, $CH_3$); 3.19 (s, 2H, $CH_2$); 6.60 (m, 1H, J=1.57 Hz, Cp-H); 6.83 (d, 1H); 6.96 (d, 1H).

Chloro(2,4,7-trimethylindenyl)dimethylsilane 7.24 g of 2,4,7-trimethylindene (45.8 mmol) were suspended in 70 ml of $Et_2O$, cooled to 0° C., and to it were added 19.2 ml of a 2.5 M BuLi solution in hexane (48.0 mmol) with stirring. A slightly yellow cream is obtained. After allowing the reaction mixture to reach ambient temperature, additional 10 ml of $Et_2O$ were added, to improve stirring. After about 1 h the mixture was cooled again to 0° C. and 7.20 g of $Me_2SiCl_2$ (55.2 mmol, 1.2 eq) in 30 ml di THF, previously cooled to 0° C., were added to it. At the end of the addition, the reaction mixture was allowed to reach ambient temperature. At this point the reaction mixture, which appeared as a white suspension, was filtered to remove LiCl, and then all solvents and excess $Me_2SiCl_2$ were removed under reduced pressure to leave 11.8 g of pale yellow oil (98% yield).

$^1H$-NMR ($CDCl_3$), ppm: 0.07 (s, 3H, Si—$CH_3$); 0.38 (s, 3H, Si—$CH_3$); 2.29 (d, 3H, J=0.98 Hz, $CH_3$ in 2); 2.36 (m, 6H, $CH_3$ in 4 and 7); 3.72 (s, 1H, CH); 6.66 (m, 1H, Cp-H); 6.84 (d, 1H, H5 or H6); 6.95 (d, 1H, H6 or H5).

(2,4,7-trimethylindenyl)(9-fluorenyl)dimethylsilane

A 2.5 M n-BuLi solution in hexane (16.80 mL, 42.00 mmol, n-BuLi:fluorene=1.04:1) was added dropwise at 0° C. under stirring to a solution of 6.70 g of fluorene (40.31 mmol) in 100 ml of $Et_2O$ in a 500 mL 3-necked round flask. The resulting orange solution was allowed to warm up to room temperature and stirred for 1 h. A solution of chloro(2,4,7-trimethylindenyl)dimethylsilane (10.05 g, 40.06 mmol) in 20 mL of THF was cooled to 0° C. and slowly added to the lithium salt solution, also previously cooled to 0° C. At the end of the addition an orange-brown suspension was obtained. The latter was allowed to warm up to room temperature and stirred for 1.5 h. Then the reaction mixture was evaporated under reduced pressure to give a brown sticky solid, which was treated at r.t. with 150 mL of toluene and finally filtered to remove LiCl. The filtrate was dried in vacuo to give 16.48 g of a reddish oil, whose $^1H$ NMR showed it to be the target compound contaminated by minor amounts of not identified by-products (crude yield quantitative). The product was used as such in the next step without further purification.

Dimethylsilyl(2,4,7-trimethyl-inden-1-yl)(9-fluorenyl)zirconium dichloride, (A-2)

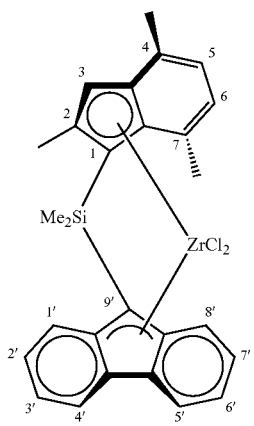

A 2.5 M n-BuLi solution in hexane (35.50 mL, 88.75 mmol) was added dropwise at 0° C. under stirring to a solution of 16.48 g of (2,4,7-trimethylindenyl)(9-fluorenyl)dimethylsilane (43.30 mmol) in 150 mL of $Et_2O$ in a 500 mL 3-necked round flask. The resulting red solution was allowed to warm up to r.t. and stirred for 1 h. Then a slurry of 10.09 g of $ZrCl_4$ (43.30 mmol) in 100 mL of toluene was prepared, cooled to 0° C. and added to the lithium salt solution, also previously cooled to 0° C. The reaction mixture was then allowed to warm up to r.t. and stirred for 2.5 h. The solvents were removed in vacuo to give a dark-red residue, which was treated at r.t. with 150 mL of toluene and then filtered on a G4 frit. The residue was further washed with toluene (3×50 mL), then dried in vacuo to give 14.36 g of a brick-red powder, whose $^1H$ NMR analysis showed it to be the desired complex. Mass balance indicates that the product contained 20.4% wt. of LiCl (yield 45.7%).

The compound is stable as powder at room temperature under nitrogen atmosphere for 2 months, but shows relevant decomposition for longer storage time. The metallocene is poorly soluble in common organic solvents, such as toluene and dichloromethane. The best solvent for NMR analysis is 1,1,2,2-tetrachloroethane-$d_2$. The NMR analysis must be performed immediately after sample preparation, because the metallocene is not stable for long time in chlorinated solvents. An aliquot of this sample (2.07 g) was dissolved into 40 mL of a mixture THF/toluene=1/3 (v/v), stirred for 15 min and filtered over a G4 frit. The filtrate was discarded, while the residue was further washed with a small volume of toluene and then dried to give ca. 1 g of an orange powder. $^1$H-NMR analysis showed it to be the pure complex, free from LiCl.

$^1$H NMR (1,1,2,2-tetrachloroethane-$d_2$), ppm: 1.41 (s, 3H, Si—$CH_3$); 1.42 (s, 3H, Si—$CH_3$); 2.17 (s, 3H, $CH_3$ in 4); 2.32 (s, 3H, $CH_3$ in 2); 2.66 (s, 3H, $CH_3$ in 7); 6.59 (d, J=6.85 Hz, H6); 6.72 (d, J=6.85 Hz, H5); 6.69 (s, 1H, H3); 6.99 (dd, J=7.63, 8.61 Hz, H7'); 7.27 (dd, J=7.63, 8.61 Hz, H2'); 7.40 (dd, J=7.63, 8.61 Hz, H6'); 7.55 (dd, J=7.63, 8.61 Hz, H3'); 7.67 (d, J=8.61 Hz, H8'); 7.73 (d, J=8.61 Hz, H1'); 7.87 (d, J=8.61 Hz, H5'); 7.91 (d, J=8.61 Hz, H4').

Example 1 and Comparative Example 3

1-butene polymerizations

The cocatalyst methylalumoxane (MAO) was a commercial product from Crompton, 10% wt/vol (1.7 M in Al) in toluene, and was used as received. The catalyst mixture was prepared by dissolving the amount of the metallocene reported in table 1 with the proper amount of the MAO solution, (Al/Zr ratio=500 mol/mol) obtaining a solution which was stirred for 10 min at room temperature before being injected into the autoclave.

6 mmol of $Al^iBu_3$ (as a 1 M solution in hexane) and 1350 g of 1-butene were charged at room temperature in a 4-L jacketed stainless-steel autoclave, equipped with magnetically driven stirrer and a 35-mL stainless-steel vial, connected to a thermostat for temperature control, previously purified by washing with an $Al^iBu_3$ solution in hexanes and dried at 50° C. in a stream of nitrogen. The autoclave was then thermostated at the polymerization temperature, and then the toluene solution containing the catalyst/cocatalyst mixture was injected in the autoclave by means of nitrogen pressure through the stainless-steel vial, and the polymerization carried out at constant temperature for the time indicated in Table 1. Then stirring is interrupted; the pressure into the autoclave is raised to 20 bar-g with nitrogen. The bottom discharge valve is opened and the 1-butene/poly-1-butene mixture is discharged into a heated steel tank containing water at 70° C. The tank heating is switched off and a flow of nitrogen at 0.5 bar-g is fed. After cooling at room temperature, the steel tank is opened and the wet polymer collected. The wet polymer is dried in an oven under reduced pressure at 70° C. Polymerization data are reported in table 1.

Example 2

Propylene Polymerization

The cocatalyst methylalumoxane (MAO) was a commercial product which was used as received (Witco AG, 10% wt/vol toluene solution, 1.7 M in Al). The catalyst mixture was prepared by dissolving the amount of the metallocene (A-1) reported in table 1 with the proper amount of the MAO solution, obtaining a solution which was stirred for 10 min at ambient temperature before being injected into the autoclave.

2 mmol of $Al^iBu_3$ (as a 1M solution in hexane) and 700 g of propylene were charged at room temperature in a 2.4-L jacketed stainless-steel autoclave, equipped with magnetically driven stirrer and a 35-mL stainless-steel vial, connected to a thermostat for temperature control, previously purified by washing with an Al(i-Bu)$_3$ solution in hexanes and dried at 50° C. in a stream of propene. The autoclave was then thermostated at the polymerization temperature, and then the toluene solution containing the catalyst/cocatalyst mixture was injected in the autoclave by means of nitrogen pressure through the stainless-steel vial, and the polymerization carried out at constant temperature for 1 hour. The polymerization was stopped by pressurizing CO into the reactor. After venting the unreacted monomer and cooling the reactor to room temperature, the polymer was dried under reduced pressure at 60° C. Polymerization data are reported in table 1.

TABLE 1

| Example | monomer | Zirconocene | mg | $Al_{(MAO)}/Zr$ | $T_p$ °C. | t min | $kg_{Polymer}/(g_{cat} \times h)$ | $M_v$ | $T_m$ °C. |
|---|---|---|---|---|---|---|---|---|---|
| 1 | 1-butene | A-1 | 3 | 500 | 70 | 60 | 14.3 | 316 400 | 96.0 (**) |
| 2 | propylene | A-1 | 1 | 500 | 70 | 60 | 38 | 152 200 | 110 |
| 3 (*) | 1-butene | A-2 | 3 | 500 | 70 | 60 | 3.3 | 156 800 | 97.0 (**) |

(*) comparative.
(**) Form II

Synthesis of dimethylsilyl(2,4,6-trimethylinden-1-yl)(9-fluorenyl)dimethylzirconium (A-1b)

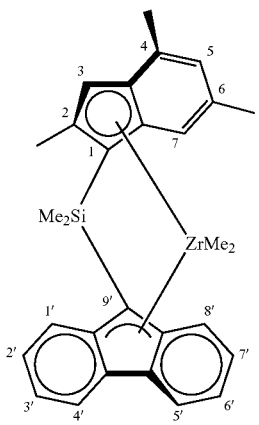

Chloro(2,4,6-trimethylindenyl)dimethylsilane

A 2.5 M n-BuLi solution in hexane (9.6 mL) was added dropwise at 0° C. under nitrogen to a solution of 3.6 g of 2,4,6-trimethylindene in 35 mL of $Et_2O$. During the addition a white-off suspension was formed. After 10 min the mixture was allowed to warm up to r.t. and stirred for 30 min, with final formation of a white suspension. Then a solution of $Me_2SiCl_2$ (4 mL) in 35 mL of THF was cooled to 0° C. and slowly added to the lithium salt suspension, also cooled to 0° C. After 30 min the yellow reaction mixture was allowed to warm up to r.t. and stirred for 24 h. Then the solvents were removed in vacuo and the light orange oil with a powder was characterized by $^1H$-NMR spectroscopy. The product was used as such in the next step without further purification.

$^1H$-NMR ($CD_2Cl_2$), ppm: 0.29 (s, 3H, Si—$CH_3$); 0.54 (s, 3H, Si—$CH_3$); 2.41 (s, 3H, 2-$CH_3$); 2.50 (s, 3H, $CH_3$); 2.52 (s, 3H, $CH_3$); 3.65 (m, 1H, CH); 6.81 (m, 1H, Cp-H); 7.00 (m, 1H); 7.26 (m, 1H).

(2,4,6-trimethylindenyl)(9-fluorenyl)dimethylsilane

A 2.5 M n-BuLi solution in hexane (9.6 mL) was added dropwise at 0° C. under stirring to a solution of 3.78 g of fluorene in 40 ml of $Et_2O$ in a 100 mL Schlenk flask. After 30 min the resulting orange solution was allowed to warm up to room temperature and stirred for 3 days. A solution of chloro (2,4,6-trimethylindenyl)dimethylsilane (22.60 mmol) in 20 mL of THF was cooled to 0° C. and slowly added to the lithium salt solution, also previously cooled to 0° C. At the end of the addition a light brown suspension was obtained. The latter was allowed to warm up to room temperature and stirred for 24 h. Then the reaction mixture was evaporated under reduced pressure to give a brown sticky solid, which was treated at r.t. with 50 mL of toluene and then filtered to remove LiCl. The filtrate was dried in vacuo to give 8.54 g of a brown oil. The product was characterized by $^1H$-NMR spectroscopy: there are the signals of two isomeric species: allylic and vinylic (2:1). The product was used as such in the next step without further purification.

$^1H$-NMR ($CD_2Cl_2$), ppm: −0.37 (s, 3H, Si—$CH_3$ allylic); −0.35 (s, 3H, Si—$CH_3$ allylic); 0.11 (s, 6H, 2 Si—$CH_3$ vinylic); 2.08 (s, 3H, 2-$CH_3$ vinylic); 2.25 (s, 3H, 2-$CH_3$ allylic); 2.35 (s, 3H, $CH_3$ allylic); 2.35 (s, 3H, $CH_3$ vinylic); 2.39 (s, 3H, $CH_3$ vinylic); 2.43 (s, 3H, $CH_3$ allylic); 3.39 (s, 1H, Flu-CH vinylic); 3.73 (s, 1H, Ind-H1); 3.96 (s, 2H, Ind-H1); 4.30 (s, 1H, Flu-CH); 6.70-7.97 (m, 21H, Ar).

Dimethylsilyl(2,4,6-trimethylinden-1-yl)(9-fluorenyl)dimethylzirconium

A 1.4 M MeLi solution in $Et_2O$ (7.5 mL) was added dropwise at −78° C. under stirring to a solution of 1.95 g of (2,4,6-trimethyl-indenyl)(9-fluorenyl)dimethylsilane in 35 mL of $Et_2O$ in a 100 mL Schlenk flask. The resulting orange-red solution was allowed to warm up to r.t. and stirred for 24 h. Then to the lithium salt solution, cooled to −78° C., was added a 1.4 M MeLi solution in $Et_2O$ (7.5 mL), before adding a slurry of 1.28 g of $ZrCl_4$ in 20 mL of toluene also cooled to −78° C. The reaction mixture was kept at −78° C. for 10 min and then allowed to warm up to r.t. and stirred for 3 h. The solvents were removed in vacuo to give a dark-brown residue, which was slurried at r.t. with 70 mL of toluene and then filtered to remove LiCl. The black extract was dried by removing the solvent under reduced pressure and was then slurried in $Et_2O$ (90 mL) and then filtered. The black residue from the filtration was further slurried in 50 mL $Et_2O$ and then filtered to give a black residue and a yellow solution. The latter was dried by removing the solvent under reduced pressure at r.t. to give 0.25 g of a yellow powder characterized by $^1H$ NMR analysis. The residue was continuously extracted (4 hours) with 50 ml of refluxing pentane, giving a yellow solution. The latter was dried in vacuo to give 0.72 g of a yellow powder. The two samples of yellow powder have the same NMR spectra and were thus combined. Isolated yield 37.9%.

$^1H$ NMR ($CD_2Cl_2$), ppm: −2.54 (s, 3H, Zr—$CH_3$); −1.34 (s, 3H, Zr—$CH_3$); 1.24 (s, 3H, Si—$Cl_3$); 1.36 (s, 3, Si—$CH_3$); 2.16 (s, 3H, 2-$CH_3$); 2.17 (s, 3H, 6-$CH_3$); 2.24 (s, 3H, 4-$CH_3$); 6.58 (s, 1H, H3); 6.86 (s, 1H, H5); 7.14 (s, 1H, m); 6.92-8.13 (m, 8H, Flu).

$^{13}C$ NMR ($CD_2Cl_2$), ppm: 3.04 ($CH_3$, Si—$CH_3$); 3.11 ($CH_3$, Si—$CH_3$); 18.47 ($CH_3$, on C2); 19.45 ($CH_3$, on C4); 21.80 ($CH_3$, on C6); 34.81 ($CH_3$, Zr—$CH_3$); 40.59 ($CH_3$, Zr—$CH_3$); 63.24 ($C9^1$); 77.75 ($C1^1$); 111.91 (C3); 122.06 (C7); 123.17 ($C6^1$); 123.56 ($C3^1$); 124.00 ($C5^1$); 124.73 ($C4^1$); 124.97 (C quat); 125.83 (C5); 125.95 ($C1^1$); 126.11 ($C7^1$); 126.21 (C quat); 126.52 ($C8^1$); 127.23 ($C2^1$); 127.97 (C quat); 129.52 (C quat); 131.77 (C quat); 133.38 (C quat); 133.45 (C quat); 133.96 (C quat).

Preparation of the Catalytic Solution.

23.2 mg of dimethylsilyl(2,4,6-trimethylinden-1-yl)(9-fluorenyl)dimethylzirconium (A-1b) were charged at room temperature under nitrogen atmosphere into a 50 mL Schlenk flask, equipped with a magnetic stirrer. 3.9 mL of MAO Albemarle 30% wt./wt. in toluene (18.6 mmol, $Al_{MAO}/Zr=400$ mol/mol) were charged at room temperature under nitrogen atmosphere into a second 50 mL Schlenk flask. Triisobutylaluminium (TIBA) in cyclohexane (18.6 mL, conc. 99 g/L, 9.3 mmol, $Al_{TIBA}/Zr=200$ mol/mol, $Al_{TOT}/Zr=600$ mol/mol, MAO/TIBA=2/1 mol/mol) was then added at room temperature to MAO, obtaining a colourless solution, which was stirred at r.t. for 1 h. Then 6.9 mL of anhydrous cyclohexane were added to this alkyl solution, achieving a concentration of 100 g of total catalyst (metallocene plus MAO plus TIBA) for each liter of solution. Finally this solution of alkyls in cyclohexane/toluene was slowly added at room temperature under nitrogen atmosphere to the metallocene, yielding after 15 min stirring a clear orange-red catalytic solution, which was tested as such in polymerization. The concentration of A-1b resulted to be 0.79 mg of metallocene per mL of solution.

Polymerizations.

Example 4

Polymerization of Butene in Bulk 6 mmol of Al$^i$Bu$_3$ (as a 1 M solution in isohexane) and 1350 g of 1-butene were charged at room temperature in a 4-L jacketed stainless-steel autoclave, equipped with magnetically driven stirrer and a 35-mL stainless-steel vial, connected to a thermostat for temperature control, previously purified by washing with an Al$^i$Bu$_3$ solution in isohexanes and dried at 50° C. in a stream of nitrogen. The autoclave was then thermostated at 70° C., and then the solution containing the catalyst/cocatalyst mixture was injected in the autoclave by means of nitrogen pressure through the stainless-steel vial, and the polymerization carried out at constant temperature for 1 h. Then stirring was interrupted; the pressure into the autoclave was raised to 20 bar-g with nitrogen. The bottom discharge valve was opened and the 1-butene/poly-1-butene mixture was discharged into a heated steel tank containing water at 70° C. The tank heating was switched off and a flow of nitrogen at 0.5 bar-g was fed. After cooling at room temperature, the steel tank was opened and the wet polymer collected. The wet polymer was dried in an oven under reduced pressure at 70° C. The results are shown in Table 2

Examples 5 and 6

Ethylene-butene Copolymerizations in Bulk

A 4.4 L jacketed stainless-steel autoclave, equipped with a magnetically driven stirrer and a 35-mL stainless-steel vial, connected to a thermostat for temperature control, was previously purified by washing with an Al$^i$Bu$_3$ solution in isohexanes and dried at 60° C. in a stream of nitrogen. The amount of monomers initially charged into the autoclave was calculated via ASPEN ONE simulation, based on the desired composition for the final copolymer and on the ethylene/butene reactivity ratio of the metallocene, defined as:

$$R = \frac{(C_2/C_4)_{polymer}}{(C_2/C_4)_{liquid\ phase}}$$

The polymerization experiments were performed by setting R=15.

The scavenger (6 mmol of Al$^i$Bu$_3$ as solution in isohexane) and the monomers in the amounts reported in Table 2 were charged at room temperature into the autoclave. The latter is then thermostated at 70° C. When pressure and temperature of the autoclave were constant, 2.6 mL of the catalytic solution prepared above containing the catalyst/cocatalyst mixture were diluted with 5 mL of cyclohexane, charged in the stainless-steel vial and injected into the autoclave by nitrogen overpressure. Ethylene was continuously fed over the whole polymerization time with a Flow Record & Control system (FRC) to maintain the pressure at the desired value. At the end of the polymerization stirring was interrupted; the pressure into the autoclave was increased with nitrogen up to 20 bar-g. The bottom discharge valve was opened and the copolymer was discharged into a heated steel tank and treated for 10 min with water steam. The tank heating was switched off and a flow of nitrogen at 0.5 bar-g was fed to remove the water. After cooling at room temperature, the steel tank was opened and the wet polymer collected. The wet polymer was dried overnight in an oven under reduced pressure at 70° C. The results are reported in Table 2

TABLE 2

| Ex | initial 1-butene (g) | initial ethylene (g) | butene in liq. phase (wt %) | ethylene in liq. phase (wt %) | MC (mg) | time (min) | adsorbed ethylene (g) | Activity (Kg/g$_{MC}$/h) | I.V. (dL/g) THN | butene (wt %) NMR | ethylene (wt %) NMR | r$_1$ × r$_2$ | T$_m$ (° C.) | T$_g$ (° C.) |
|---|---|---|---|---|---|---|---|---|---|---|---|---|---|---|
| 4 | 1350 | 0 | 100 | 0 | 3.95 | 60 | 0 | 11.2 | 1.98 | 100 | 0 | | 97.0 | n.a. |
| 5 | 1344 | 11.8 | 99.26 | 0.74 | 2.05 | 92 | 9.1 | 36.5 | 1.71 | 90.9 | 9.1 | 0.70 | n.a. | −41.8 |
| 6 | 1336 | 18.5 | 98.84 | 1.16 | 2.05 | 60 | 23.8 | 94.3 | 2.24 | 86.2 | 13.8 | 0.66 | n.a. | −47.1 | n.a. = not available

The invention claimed is:

1. A process for preparing 1-butene polymers, comprising polymerizing 1-butene or copolymerizing 1-butene with ethylene, propylene or an alpha-olefin of formula CH$_2$=CHT wherein T is a C$_3$-C$_{10}$ alkyl group, in the presence of a catalyst system obtained by contacting:

A) a metallocene compound belonging to formula (I):

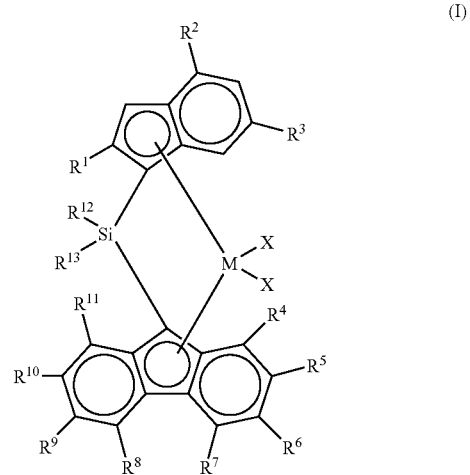

(I)

wherein

M is zirconium, titanium or hafnium;

X, equal to or different from each other, is a hydrogen atom, a halogen atom, an R, OR, OR'O, $OSO_2CF_3$, $OCOR$, SR, $NR_2$ or $PR_2$ group wherein R is a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing heteroatoms belonging to groups 13-17 of the Periodic Table of the Elements, and R' is a $C_1$-$C_{20}$-alkylidene, $C_6$-$C_{20}$-arylidene, $C_7$-$C_{20}$-alkylarylidene, or $C_7$-$C_{20}$-arylalkylidene radical;

$R^4$, $R^5$, $R^6$, $R^7$, $R^8$, $R^9$, $R^{10}$, and $R^{11}$, equal to or different from each other, are hydrogen atoms, or $C_1$-$C_{40}$ hydrocarbon radicals optionally containing heteroatoms belonging to groups 13-17 of the Periodic Table of the Elements; at least two $R^4$, $R^5$, $R^6$, $R^7$, $R^8$, $R^9$, $R^{10}$, and $R^{11}$ can also optionally join to form at least one $C_4$-$C_{10}$ condensed saturated or unsaturated ring;

$R^{12}$ and $R^{13}$, equal to or different from each other, are hydrogen atoms or $C_1$-$C_{40}$ hydrocarbon radical optionally containing heteroatoms belonging to groups 13-17 of the Periodic Table of the Elements; and $R^1$ is a linear or branched, $C_1$-$C_{20}$-alkyl radicals, optionally containing heteroatoms belonging to groups 13-17 of the Periodic Table of the Elements;

$R^2$ and $R^3$, equal to or different from each other, are linear $C_1$-$C_{20}$-alkyl radicals, optionally containing heteroatoms belonging to groups 13-17 of the Periodiv Table of the Elements;

B) an alumoxane or a compound that forms an alkyl metallocene cation; and optionally C) an organo aluminum compound.

2. The process according to claim 1 wherein in the compound of formula (I), $R^1$, $R^2$ and $R^3$, equal to or different from each other, are $C_1$-$C_{10}$-alkyl radicals; X is a hydrogen atom, a halogen atom, an OR'O or R group; $R^4$, $R^5$, $R^6$, $R^7$, $R^8$, $R^9$, $R^{10}$, and $R^{11}$ are hydrogen atoms; and $R^{12}$ and $R^{13}$ are $C_1$-$C_{10}$ alkyl or $C_6$-$C_{20}$ aryl radicals.

3. The process according to claim 1 wherein said process is carried out in liquid phase, optionally in the presence of an inert hydrocarbon solvent.

4. The process according claim 1 wherein 1-butene is homopolymerized.

5. The process according to claim 1 wherein the comonomer are selected from ethylene, propylene and 1-hexene.

6. A process for the polymerization of alpha olefins comprising contacting, under polymerization conditions, at least one alpha olefin with a catalyst system obtained by contacting:

A) a metallocene compound of formula (I):

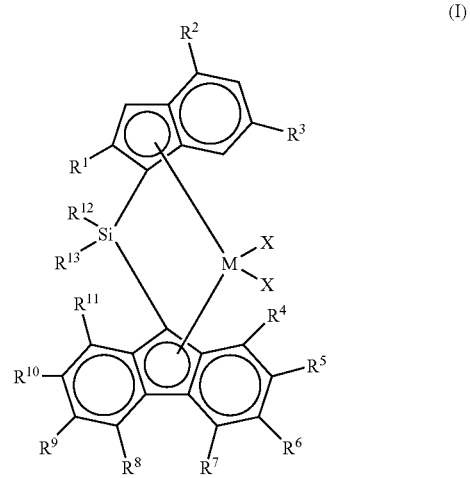

wherein

M is zirconium, titanium or hafnium;

X, equal to or different from each other, is a hydrogen atom, a halogen atom, an R, OR, OR'O, $OSO_2CF_3$, OCOR, SR, $NR_2$ or $PR_2$ group wherein R is a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing heteroatoms belonging to groups 13-17 of the Periodic Table of the Elements, and R' is a $C_1$-$C_{20}$-alkylidene, $C_6$-$C_{20}$-arylidene, $C_7$-$C_{20}$-alkylarylidene, or $C_7$-$C_{20}$-arylalkylidene radical;

$R^4$, $R^5$, $R^6$, $R^7$, $R^8$, $R^9$, $R^{10}$, and $R^{11}$, equal to or different from each other, are hydrogen atoms, or $C_1$-$C_{40}$ hydrocarbon radicals optionally containing heteroatoms belonging to groups 13-17 of the Periodic Table of the Elements; two or more $R^4$, $R^5$, $R^6$, $R^7$, $R^8$, $R^9$, $R^{10}$, and $R^{11}$ can also optionally join to form at least one $C_4$-$C_{10}$ condensed saturated or unsaturated ring;

$R^{12}$ and $R^{13}$, equal to or different from each other, are hydrogen atoms or $C_1$-$C_{40}$ hydrocarbon radicals optionally containing heteroatoms belonging to groups 13-17 of the Periodic Table of the Elements; and $R^1$ is a linear or branched $C_1$-$C_{20}$-alkyl radical, optionally containing heteroatoms belonging to groups 13-17 of the Periodic Table of the Elements;

$R^2$ and $R^3$, equal to or different from each other, are linear $C_1$-$C_{20}$-alkyl radicals, optionally containing heteroatoms belonging to groups 13-17 of the Periodic Table of the Elements;

B) an alumoxane or a compound that forms an alkyl metallocene cation; and optionally C) an organo aluminum compound.

* * * * *